(12) United States Patent
Ziegler

(10) Patent No.: US 8,703,092 B2
(45) Date of Patent: Apr. 22, 2014

(54) TYPE SEPARATION OF SINGLE-WALLED CARBON NANOTUBES VIA TWO-PHASE LIQUID EXTRACTION

(75) Inventor: Kirk Jeremy Ziegler, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1121 days.

(21) Appl. No.: 12/066,301

(22) PCT Filed: Sep. 15, 2006

(86) PCT No.: PCT/US2006/036033
§ 371 (c)(1),
(2), (4) Date: May 20, 2008

(87) PCT Pub. No.: WO2008/057070
PCT Pub. Date: May 15, 2008

(65) Prior Publication Data
US 2010/0166637 A1    Jul. 1, 2010

Related U.S. Application Data

(60) Provisional application No. 60/718,028, filed on Sep. 15, 2005.

(51) Int. Cl.
*B01D 11/02* (2006.01)
*C01B 31/02* (2006.01)
*B82Y 40/00* (2011.01)

(52) U.S. Cl.
USPC ........... 423/460; 210/638; 210/749; 423/461; 977/745; 977/748; 977/751; 977/845; 977/847

(58) Field of Classification Search
USPC ......... 210/634, 635, 638, 639, 656, 702, 708, 210/723, 738, 749, 806; 423/445 R, 423/447.1–447.3, 460, 461, 445 B, 447.7; 977/742–754, 842–848; 428/367; 204/450, 451, 554, 600, 601; 209/1, 209/155
See application file for complete search history.

(56) References Cited

U.S. PATENT DOCUMENTS 6,183,714 B1    2/2001  Smalley et al.
7,074,310 B2 *  7/2006  Smalley et al. ............... 204/450
(Continued)

FOREIGN PATENT DOCUMENTS

WO    WO 02/079082       10/2002
WO    WO 2005/012172 A2   2/2005

OTHER PUBLICATIONS

Strano et al, "Electronic Structure Control of Single-Walled Carbon Nanotube Functionalization", Sep. 12, 2003, Science, vol. 301, pp. 1519-1522.*

(Continued)

*Primary Examiner* — Joseph Drodge
(74) *Attorney, Agent, or Firm* — Saliwanchik, Lloyd & Eisenschenk

(57) ABSTRACT

The subject invention provides a two-phase liquid-liquid extraction process that enables sorting and separation of single-walled carbon nanotubes based on (n, m) type and/or diameter. The two-phase liquid extraction method of the invention is based upon the selective reaction of certain types of nanotubes with electron withdrawing functional groups as well as the interaction between a phase transfer agent and ionic moieties on the functionalized nanotubes when combined in a two-phase liquid solution. Preferably, the subject invention enables efficient, bulk separation of metallic/semi-metallic nanotubes from semi-conducting nanotubes. More preferably, the subject invention enables efficient, bulk separation of specific (n, m) types of nanotubes.

23 Claims, 8 Drawing Sheets

(56) References Cited

U.S. PATENT DOCUMENTS

| | | | |
|---|---|---|---|
| 7,074,980 B2* | 7/2006 | Prato et al. | 585/839 |
| 7,250,147 B2* | 7/2007 | Tour et al. | 423/447.1 |
| 7,374,649 B2* | 5/2008 | Jagota et al. | 204/456 |
| 7,374,685 B2* | 5/2008 | Sun | 210/639 |
| 7,404,928 B2* | 7/2008 | Foos et al. | 422/82.02 |
| 7,488,876 B2* | 2/2009 | Jung et al. | 423/445 B |
| 7,572,426 B2* | 8/2009 | Strano et al. | 423/447.1 |
| 7,578,941 B2* | 8/2009 | Ziegler et al. | 210/639 |
| 7,781,635 B1* | 8/2010 | Sutto et al. | 585/836 |
| 7,939,047 B2* | 5/2011 | Tour et al. | 423/460 |
| 2003/0168385 A1* | 9/2003 | Papadimitrakopoulos | 209/1 |
| 2003/0173985 A1 | 9/2003 | Cole et al. | |
| 2004/0040834 A1* | 3/2004 | Smalley et al. | 204/164 |
| 2004/0232073 A1* | 11/2004 | Papadimitrakopoulos | 210/634 |
| 2005/0069480 A1 | 3/2005 | Huang et al. | |
| 2006/0115640 A1* | 6/2006 | Yodh et al. | 428/221 |
| 2008/0213162 A1* | 9/2008 | Smalley et al. | 423/447.7 |
| 2008/0260616 A1* | 10/2008 | Tour et al. | 423/447.1 |

OTHER PUBLICATIONS

Burghard et al, "Chemically Functionalized Carbon Nanotubes", 2005, Small, vol. 1, No. 2, pp. 180-192.*

Maeda et al, Large-Scale Separation of Metallic and Semiconducting Single-Walled Carbon Nanotubes, Jul. 1, 2005, Journal American Chemical Society, vol. 127, pp. 10287-10290.*

Chattopadhyay et al, "A Route for Bulk Separation of Semiconducting from Metallic Single-Wall Carbon Nanotubes", 2003, Journal American Chemical Society, vol. 125, pp. 3370-3375.*

Dyke et al, "Covalent Functionalization of Single-Walled Carbon Nanotubes for Materials Applications", The Journal of Physical Chemistry, vol. 108, No. 51, Dec. 23, 2004.*

Banerjee et al, "Selective Metallic Tube Reactivity in the Solution-Phase Osmylation of Single-Walled Carbon Nanotubes", Journal of American Chemical Society, vol. 126, pp. 2073-2081, Published on the Web Jan. 27, 2004.*

Bachilo, S. et al., "Structure-Assigned Optical of Single-Walled Carbon Nanotubes," *Science*, 2002, vol. 298, pp. 2361-2365.

Banerjee, S. et al., "Demonstration of Diameter-Selective Reactivity in the Sidewall Ozonation of SWNTs by Resonance Raman Spectroscopy," *Nano Letters*, 2004, vol. 4, No. 8, pp. 1445-1450.

Banerjee, S. et al., "Rational Sidewall Functionalization and Purification of Single-walled Carbon Nanotubes by Solution-phase Ozonolysis," *Journal of Physical Chemistry B* 2002, vol. 106, No. 47, pp. 12144-12151.

Dyke, C. A., et al., "Diazonium-Based Functionalization of Carbon Nanotubes: XPS and GC-MS Analysis and Mechanistic Implications", *Synlett*, pp. 155-160, No. 1.

Katz, E., et al., "Biomolecule-Functionalized Carbon Nanotubes: Applications in Nanobioelectronics", *ChemPhysChem*, 2004, pp. 1084-1104, vol. 5, No. 8.

Liang, F., et al., "A Convenient Route to Functionalized Carbon Nanotubes", *Nano Letters*, 2004, pp. 1257-1260, vol. 4, No. 7.

Ravindran, S., et al., "Functionalization of Carbon Nanotubes for Self Assembly Applications", *Materials Research Society Symposium Proceedings*, 2003, pp. 95-99, vol. 773.

Yakobson, B. I. et al., "Fullerene nanotubes: $C_{1,000,000}$ and beyond," *American Scientist*, Jul.-Aug. 1997, vol. 85, No. 4, pp. 324-337, Abstract Only.

\* cited by examiner

TYPE SEPARATION OF SINGLE-WALLED CARBON NANOTUBES VIA TWO-PHASE LIQUID EXTRACTION

CROSS-REFERENCE TO A RELATED APPLICATION

This application is a National Stage Application of International Application Number PCT/US2006/036033, filed Sep. 15, 2006; which claims the benefit of U.S. Provisional Application Ser. No. 60/718,028, filed Sep. 15, 2005, in their entirety.

FIELD OF THE INVENTION

The present invention relates generally to single-walled carbon nanotubes (SWNTs), and more particularly to materials and methods for SWNT separation by (n, m) type, as well as new devices and methods of use derived from such separated SWNTs.

BACKGROUND OF THE INVENTION

Single-wall carbon nanotubes, also commonly known as "buckytubes," have unique properties, including high strength, stiffness, thermal and electrical conductivity. SWNTs are hollow, tubular fullerene molecules consisting essentially of $sp^2$-hybridized carbon atoms typically arranged in hexagons and pentagons. SWNTs typically have diameters in the range of about 0.5 nanometers (nm) and about 3.5 nm, and lengths usually greater than about 50 nm. Background information on SWNTs can be found in B. I. Yakobson and R. E. Smalley, "Fullerene Nanotubes: $C_{1,000,000}$ and Beyond," *American Scientist*, 85:324-337 (1997) and Dresselhaus et al., *Science of Fullerenes and Carbon Nanotubes*, San Diego: Academic Press, Ch. 19, (1996) (hereinafter referred to as "Dresselhaus").

The diameter and conformation of SWNTs can be described using the system of nomenclature described by Dresselhaus. Single-wall tubular fullerenes are distinguished from each other by a double index (n, m), where n and m are integers that describe how to cut a single strip of hexagonal graphite such that its edges join seamlessly when the strip is wrapped onto the surface of a cylinder. When the resultant tube is said to be of the "armchair" or (n, n) type, since when the tube is cut perpendicularly to the tube axis, only the sides of the hexagons are exposed and their pattern around the periphery of the tube edge resembles the arm and seat of an armchair repeated n times. When m=0, the resultant tube is said to be of the "zig-zag" or (n, 0) type, since when the tube is cut perpendicular to the tube axis, the edge is a zig-zag pattern. Where n≠m and m≠0, the resulting tube has chirality and contains a helical twist to it, the extent of which is dependent upon the chiral angle.

The electronic properties of SWNTs are dependent on the conformation. For example, armchair tubes are metallic and have extremely high electrical conductivity. All single-wall carbon nanotubes can be categorized as metallic, semi-metals, or semiconducting depending on their conformation. For clarity and conciseness, both metallic tubes and semi-metal tubes will be referred to collectively as metallic nanotubes. For single-wall carbon nanotubes, about one-third of the tubes are metallic and about two-thirds are semiconducting. Metallic (n, m)-type nanotubes are those that satisfy the condition: 2n+m=3q, or n−m=3q where "q" is an integer. Metallic nanotubes are conducting with a zero band gap in energy states. Nanotubes not satisfying either condition are semiconducting and have an energy band gap. Generally, semiconducting nanotubes with smaller diameters have larger energy band gaps. Regardless of tube type, all SWNTs have extremely high thermal conductivity and tensile strength.

The particular nanotube diameter and conformation affects the physical and electronic properties of the single-wall carbon nanotube. For example, the strength, stiffness, density, crystallinity, thermal conductivity, electrical conductivity, absorption, magnetic properties, response to doping, utility as semiconductors, optical properties such as absorption and luminescence, utility as emitters and detectors, energy transfer, heat conduction, reaction to changes in pH, buffering capacity, sensitivity to a range of chemicals, contraction and expansion by electrical charge or chemical interaction, nanoporous filtration membranes and many more properties are affected by the diameter and conformation of the single-wall carbon nanotube.

From an electronics perspective, separation of SWNTs according to type (metallic versus semiconducting) may be critical for certain applications such as the construction of quantum wires, while separation by diameter for semiconducting SWNTs may be of paramount importance in the microelectronics or optical arena (e.g., because diameter governs their band-gap).

One recent approach which permits the selective preservation of the semiconducting types of nanotubes in bundles, or "ropes," of aligned single-walled carbon nanotubes has been demonstrated by IBM Corp. In that method, ropes of nanotubes of random chiralities are deposited on a silicon wafer that is then covered by a dense array of source, drain and gate connections in order to form field-effect devices. Subsequently, a voltage is applied over the nanotube ropes blowing out and destroying the metallic tubes, but leaving the semiconducting type unscathed. Thus, the surviving semiconducting nanotubes are available and still affixed as ropes to the contacts, where they may be utilized to produce active devices. However, the method provides no means of physically segregating or sorting the nanotubes into separate assemblies or containers. Nor does it provide a means for accumulating the highly conductive nanotubes as well as the metallic nanotubes.

Selective functionalization of metallic SWNTs has been disclosed, wherein selective functionalization occurs with individual nanotubes wrapped in surfactant molecules. However, separation of functionalized from the unfunctionalized nanotubes by selective solubility, sedimentation, or centrifugation has not yielded feasible separation processes. All of these rely heavily on the premise that stabilized nanotubes should remain in the supernatant while nonstabilized nanotubes should have significant aggregation allowing efficient separation. However, hydrodynamic instabilities will result in the contact of nonstabilized nanotubes (unfunctionalized) with stabilized nanotubes (functionalized) during sedimentation. This contact leads to both functionalized and unfunctionalized becoming trapped in irreversible aggregates as agglomeration is induced through sedimentation, limiting the effectiveness of the separations.

Chromatography may possibly be able to offer some separation of nanotubes by type but these suspensions are inherently instable, thereby affecting the absorption/desorption process critical to effect nanotube separations. Electrophoresis can be utilized to obtain a degree of nanotube separation while DNA-based chromatography techniques have also achieved a limited degree of nanotube separation. The major problem with these techniques is that they are only analytical-scale techniques and cannot produce large, significant quantities of nanotubes of a specific type.

While a method for separating and sorting single-wall carbon nanotubes of a specific type is desired in order to capture the desired properties of the selected nanotube type or types, such a method is complicated by two major factors. First is the nanotubes' extreme lack of dispersibility in water and most common solvents. Second, as described earlier, is the strong propensity of single-wall carbon nanotubes to "rope" together in bundles that are strongly held together by van der Waals forces. The roping phenomenon aggregates different types of single-wall carbon nanotubes together in aligned bundles or "ropes" and holds them together with a sizable tube-to-tube binding energy of up to about 500 eV/micron. These aggregates generally contain random mixtures of metallic and semiconducting types of nanotubes with assorted diameters. When electrically contacted while in bundled aggregates, the carbon nanotubes experience sizable perturbations from their otherwise pristine electronic structure that complicates the differentiation between different types of nanotubes. Also, attempts to exploit the chemical diversity within mixtures of nanotubes, either through sidewall functionalization or end-group derivatization have not been successful in separating nanotubes of specific conformations, but have produced largely bundles of nanotubes or nanotubes with significantly altered electronic properties.

No effective process for making single-wall carbon nanotubes is known whereby significant quantities of carbon nanotubes of a specific (n, m) type can be extracted after production/manufacture. Macroscopic amounts of type-sorted single-wall carbon nanotubes that would provide the broadest range of possible nanotube properties and applications are heretofore unknown.

The lack of any viable type separation of nanotubes has precluded their use in a multitude of commercial applications. The ability to separate single-walled carbon nanotubes by their type will be vital to a multitude of applications. The different types of nanotubes can be easily integrated into a wide variety of microelectronic devices, energy applications, and optical sensors. For example, metallic nanotubes can be constructed into quantum wires which will supply low energy-loss, high-throughput wires for energy savings and applications. Semiconductor nanotubes can be utilized in the formation of field-effect transistors in microelectronics or as implantable biosensors. Even the less ambitious goal of separating the metallic nanotubes from the semiconducting nanotubes will be a significant advance that will enable many new applications.

BRIEF SUMMARY OF THE INVENTION

This invention relates to two-phase liquid extraction methods for sorting and separating nanotubes, and in particular single-walled carbon nanotubes (SWNTs), by (n, m) type and/or diameter. The invention also relates to compositions of selected nanotube types and sensing devices comprising them. According to the subject invention, nanotubes are separated into target populations using phase transfer extraction methods.

In one embodiment, target nanotube populations are separated using phase transfer catalysis. Preferably, target nanotube populations are separated based on electronic properties. The method comprises mixing a population of functionalized nanotubes with a two-phase liquid solution (e.g., polar/non-polar solvents), and employing a means for inducing the transfer of functionalized nanotubes by type across the interface of the two phases.

The transfer of functionalized nanotubes may be accomplished using known properties associated with the coupling of the functionalized nanotubes with the phase transfer catalyst/agent (i.e. functionalized nanotube—inducing means interaction). For example, ionic or electrostatic interactions of the functionalized nanotubes with the inducing means may be used to affect the transfer of the desired functionalized nanotubes across the interface of the two phases. Other interactions, such as hydrophobic interactions, hydrophilic interactions, hydrogen bonding, physisorption, chemisorption, and non-covalent interactions may also be utilized to identify the desired functionalizing groups and inducing means for separating the functionalized nanotubes. In some cases, the functionalization may also be the inducing means.

In a related embodiment, a method is provided for selective extraction of metallic and semi-metallic nanotubes, preferably SWNTs, from a mixed nanotube population of semiconducting and metallic/semi-metallic nanotubes. The method comprises (a) dispersing a population of SWNTs in a polar solvent to form a polar phase; (b) selectively functionalizing SWNTs based on electronic properties by reacting selective functionalizing groups with a population of SWNTs, wherein the selective functionalizing groups bind to a target subpopulation of SWNTs; (c) adding an active moiety to the selective functionalizing group bound to the target subpopulation of SWNTs, wherein the active moiety enables separation of target subpopulation of SWNTs from remaining population of SWNTs; (d) combining the polar phase with a non-polar phase, wherein the non-polar phase comprises a phase transfer agent and a non-polar solvent; and (e) agitating the two-phase solution to effect the transport of selectively functionalized SWNTs into the non-polar phase wherein the phase transfer catalyst couples to the active moiety enabling the functionalized SWNTs to disperse in a non-polar solvent while leaving a majority of the non-functionalized SWNTs in the polar phase.

In another embodiment of the invention, a method is provided for separating SWNTs by diameter to form a diameter-separated population of SWNTs. The method comprises (a) dispersing SWNTs in a polar solvent to form a polar phase; (b) selectively functionalizing according to SWNT diameter by reacting selective functionalizing groups with a population of SWNTs, wherein the selective functionalizing groups bind to a target subpopulation of SWNTs; (c) adding an active moiety onto the sidewall of functionalized SWNTs, wherein the active moiety enables separation of functionalized SWNTs from unfunctionalized population of SWNTs; (d) combining the polar phase with a non-polar phase, wherein the non-polar phase comprises a phase transfer agent and a non-polar solvent; and (e) agitating the two-phase solution to effect the transport of functionalized SWNTs into the non-polar phase wherein the phase transfer catalyst couples to the active moiety enabling the functionalized SWNTs to disperse in a non-polar solvent while leaving a majority of the non-functionalized SWNTs in the polar phase.

In another embodiment of the invention, a method is provided for separating SWNTs of specific (n, m) type from a mixture of multiple (n, m) types of SWNTs. The method comprises (a) dispersing SWNTs in a polar solvent to form a polar phase; (b) selectively functionalizing according to SWNT (n, m) type by reacting selective functionalizing groups with a population of SWNTs, wherein the selective functionalizing groups bind to a target subpopulation of SWNTs; (c) adding an active moiety onto the sidewall of functionalized SWNTs, wherein the active moiety enables separation of functionalized SWNTs from unfunctionalized population of SWNTs; (d) combining the polar phase with a non-polar phase, wherein the non-polar phase comprises a phase transfer agent and a non-polar solvent; and (e) agitating the two-phase solution to effect the transport of functionalized SWNTs into the non-polar phase wherein the phase transfer catalyst couples to the active moiety enabling the functionalized SWNTs to disperse in a non-polar solvent while leaving a majority of the non-functionalized SWNTs in the polar phase.

Accordingly, the subject invention provides a means for achieving the separation of nanotubes by every (n,m) type, i.e., electrical properties of the nanotubes. The separation of metallic (n−m=3q) from semiconducting nanotubes is a significant achievement allowing the use of metallic nanotubes in energy applications and semiconducting nanotubes in microelectronic, optic, and sensor applications. Furthermore, the methods described herein are easily scalable and the resultant separated SWNTs are easily collected and purified to a pristine state.

According to the subject invention, by reacting an aqueous solution of selectively functionalized nanotubes with an active moiety in a two phase system, the selectively functionalized nanotubes are readily separated from the non-functionalized nanotubes. This separation occurs since the boundary between the two phases offers an increased barrier to the dispersion of unfunctionalized nanotubes in the non-polar (or organic) phase.

The active moiety required for SWNT separation/extraction into a specific phase can be chemically added to the selective functionalizing group (e.g., diazonium reagent) either before or after reaction with the nanotube sidewall. After selective functionalization of SWNTs, the nanotubes are extracted by type using a non-polar solvent comprising a phase transfer agent, such as tetraoctylammonium bromide (TOAB). The mechanism of phase transfer is due to the $TOA^+$ coupling with an anion on the aryl functional group (such as a sulfonate anion) via a one-to-one electrostatic interaction. Once sufficient $TOA^+$ has complexed with the SWNTs to render them organophilic, they can be extracted into the organic phase. Preferably, the two-phase is shaken vigorously to increase interfacial area and assist nanotube transfer across the interface.

BRIEF DESCRIPTION OF THE DRAWINGS

Referring now to the exemplary drawings wherein like elements are numbered alike in the several Figures.

DETAILED DESCRIPTION OF THE INVENTION

Figure 1:
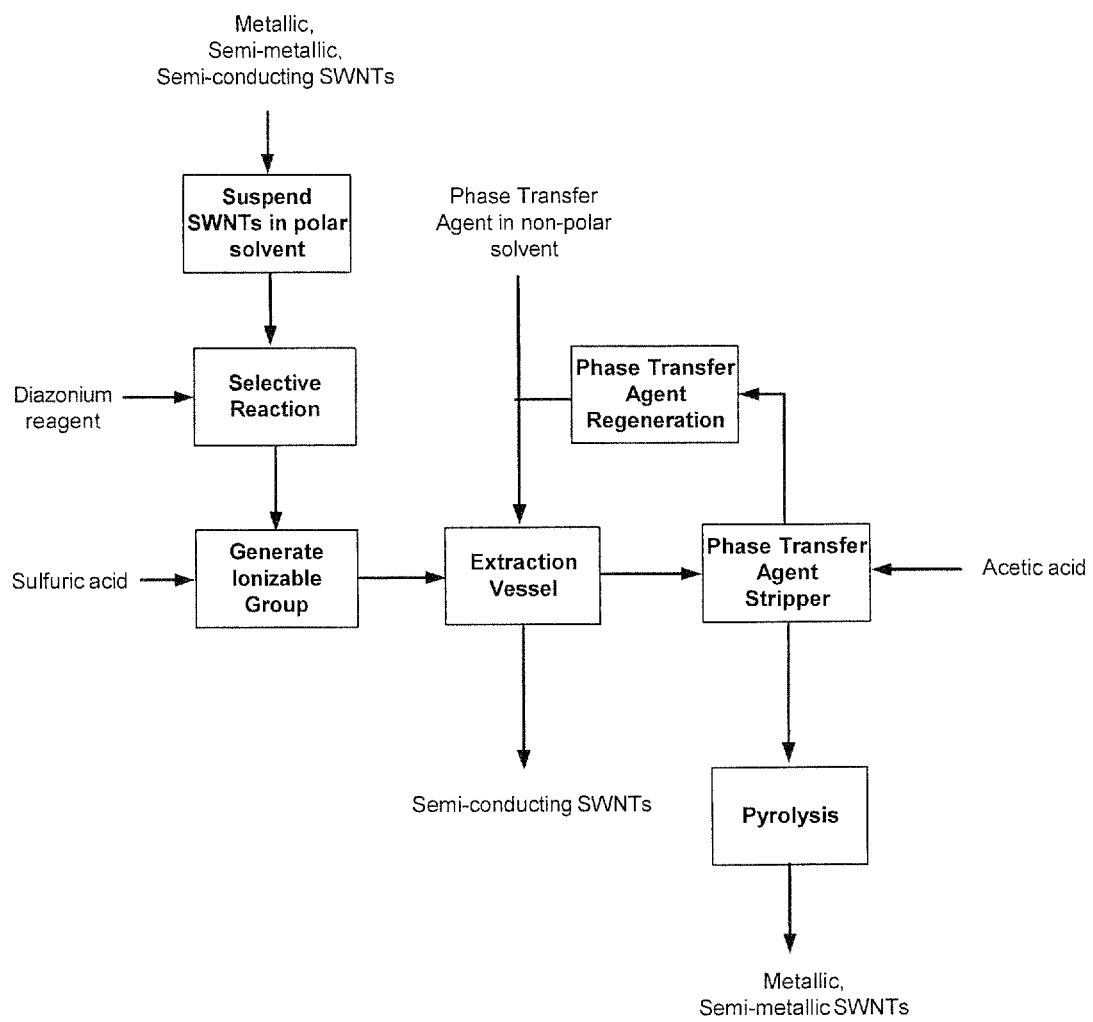
FIG. 1 is a schematic diagram of a two-phase liquid separation and extraction in accordance with the subject invention.

This invention relates to methods for sorting and separating nanotubes, preferably single-walled carbon nanotubes, utilizing phase transfer methods. In certain embodiments of the invention, electronic properties, chirality, and/or diameter dimensions of the nanotubes are exploited to affect the separation of target nanotube populations into a desired phase for extraction.

Preferred methods for nanotube sorting, separation, and extraction are based on two-phase liquid extraction. In certain embodiments of the invention, a population of SWNTs (generally containing a mixture of nanotubes having different diameters and different conductivities) is suspended in a polar solvent (using surfactants or polymers) to form a polar phase; selectively functionalized with active moieties allowing for separation and extraction by type; combining the polar phase with a non-polar phase comprising a phase transfer agent to form a two-phase liquid solution; and agitating the two-phase solution to effect the transport of selectively functionalized nanotubes across the two-phase interface into the non-polar phase.

According to the subject invention, carbon nanotubes are elongated tubular bodies that are composed of a plurality of cylindrically rolled graphite films that are arranged telescopically. Nanotubes of the invention can be either single-walled carbon nanotubes (SWNTs), few wall nanotubes (FWNTs), or multi wall nanotubes (MWNTs). A preferred nanotube is a single-walled carbon nanotube. Single-walled carbon nanotubes can further be subdivided into metallic and/or semi-metallic SWNTs or semiconducting SWNTs.

Nanotubes of the subject invention are primarily carbon, although the nanotube fiber may have a number of other atoms, such as boron, nitrogen, and the like. The raw material carbon used to produce nanotubes may be fullerenes, metallofullerenes, graphite, including carbon black, carbon monoxide, hydrocarbons, including paraffins, olefins, diolefins, ketones, aldehydes, alcohols, ethers, aromatic hydrocarbons, diamonds, another compound that comprises carbon, or a combination comprising one or more of the foregoing raw materials. Specific hydrocarbons useful for forming carbon nanotubes include methane, ethane, propane, butane and higher paraffins and isoparaffins, ethylene, propylene, butene, pentene and other olefins and diolefins, ethanol, propanol, acetone, methyl ethyl ketone, acetylene, benzene, toluene, xylene, ethylbenzene, benzonitrile, and combinations comprising one or more of the foregoing materials.

Nanotubes of the invention may have diameters of about 1 nanometer for a single wall nanotube to about 50 nm for a few wall and/or multi wall nanotube. The nanotubes may have a length of about 1 nm to about 1 centimeter (cm) or greater.

In some embodiments, nanotubes are subjected to chemical reaction pathways in which selective covalent functionalization occurs as a result of nanotube electronic structure. Selective functionalization can be accomplished via covalent or non-covalent bonding. According to the subject invention, selective functionalization of metallic/semi-metallic nanotubes is accomplished by reacting a population of SWNTs with selective functionalizing groups (such as electron withdrawing moieties). As understood by the skilled artisan, selective functionalization of nanotubes in accordance with the subject invention can be accomplished in any media including, for example, liquid, solid, or gas. Preferably, the nanotubes are selectively functionalized in a liquid medium.

In a preferred embodiment of the invention, the selective functionalizing groups selective for metallic/semi-metallic nanotubes are diazonium salts. When electron withdrawing functional groups are reacted with a population of SWNTs, covalent aryl bonds form on metallic/semi-metallic SWNT sidewalls when electrons are withdrawn from the nanotubes. Such selective nanotube functionalization enables highly selective and scalable sorting as well as separation of metallic/semi-metallic nanotubes from semiconducting SWNTs.

Examples of how to prepare diazonium salts are disclosed in U.S. Pat. Nos. 3,867,147 and 3,849,392. Contemplated diazonium salts for use in methods of the invention include, but are not limited to, alkoxy-substituted or alkoxy free aromatic and non-aromatic diazonium salts, with various substituents attached to the salt, including the aromatic rings.

Diazonium salts that can be used in accordance with the subject invention include, but are not limited to, alkoxy containing diphenylamine-4-diazonium salts (such as diazonium salts derived from the following amines: 4-amino-3-methoxydiphenylamine, 4-amino-2-methoxydiphenylamine, 4'-amino-2-methoxydiphenylamine, 4'-amino-4-methoxydiphenylamine, 4-amino-3-ethoxydiphenylamine, 4-amino-3-hexyloxydi-phenylamine, 4-amino-3-.beta.-hydroxyethoxydiphenylamine, 4'-amino-2-methoxy-5-methyldiphenylamine, 4-amino-3-methoxy-6-methyldiphenylamine, 4'-amino-4-n-butoxydiphenylamine and 4'-amino-3',4-dimethoxydiphenylamine); methoxy-substituted aromatic diazonium salts (such as 2,3',5-trimethoxydiphenyl-4-diazonium chloride; 2,4',5-triethoxydiphenyl-4-diazonium chloride; 4-(3-(3-methoxyphenyl)-propylamino)-benzenediazonium sulfate; 4-(N-ethyl-N-(4-methoxybenzyl)-amino)-benzenediazonium chloride; 4-(N-(naphthyl-(2)methyl)-N-n-propylamino) methoxybenzenediazonium sulfate, 4-(N-(3-phenoxypropyl)-N-methylamino)-2,5-dimethoxybenzenediazonium tetrafluoroborate; 4-(N-(3-phenylmercaptopropyl)-N-ethylamino)-2-chloro-5-methoxybenzenediazonium chloride; 4-(4-(3-methylphenoxy)-phenoxy)-2,5-dimethoxybenzenediazonium sulfate; 4-(4-methoxyphenylmercapto)-2,5-diethoxy-benzenediazonium chloride; 2,5-diethoxy-4-phenoxybenzenediazonium chloride; 4-(3,5-dimethoxybenzoylamino)-2,5-diethoxybenzenediazonium hexafluorophosphate; meth-oxycarbazole-3diazonium chloride; 3-methoxy-diphenyleneoxide-2-diazonium chloride and methoxydiphenylamine-4-diazonium sulfate); alkoxy-free aromatic diazonium salts (such as 4-diazodiphenylamine sulfate; diphenyl-4-diazonium chloride; 2-4-(N-(naphthyl2-methyl)-N-propylamino)benzenediazonium sulfate; chlorodiphenyl-4-diazonium chloride; 4-(3-phenylpropylamino)-benzenediazonium sulfate; 4-(N-ethyl-N-(benzyl)-amino)-benzenediazonium chloride; 4-(N,N-dimethylamino)-benzenediazonium tetrafluoroborate; 4-(N-(3-phenylmercaptopropyl)-N-ethyl-amino)-2-chlorobenzene-diazonium chloride; 4-(4methylphenoxy)benzenediazonium sulfate; 4-(phenylmercapto)-benzenediazonium chloride; 4-phenoxybenzenediazonium chloride; 4-(benzoylamino)-benzenediazonium hexafluorophosphate; methylcarbazole-3-diazoniumchloride; 3-methyldiphenyleneoxide-2diazoniumchloride and 3-methyldiphenylamine-4-diazonium sulfate); and alkoxy free diarylamine-4-diazonium salts (such as diphenylamine-4-diazonium salts that include, for example, the diazonium salts derived from the following amines: 4-amino-diphenylamine, 4-amino-3-methyl-diphenylamine, 4-amino-3-ethyldi-phenylamine, 4'-amino-3-methyl-diphenylamine, 4'-amino-4-methyldiphenylamine, 4'-amino-3,3'-dimethyldiphenylamine, 3'-chloro-4-amino-diphenylamine, 4-aminodi-phenylamine-2-sulfonic acid, 4-aminodiphenylamine-2-carboxylic acid, 4-aminodiphenylamine-2'-carboxylic acid and 4'-bromo-4-aminodiphenylamine).

According to the subject invention, SWNTs are dispersed in a polar solvent to form a polar phase. Methods for enabling SWNT dispersibility in a polar solvent include subjecting SWNTs to chemical reaction pathways involving surfactants and/or polymers. As understood by the skilled artisan, the SWNTs can be functionalized and dispersed in any phase and transferred across a system boundary to another immiscible phase. For example, the SWNTs can be functionalized and dispersed in a non-polar phase, wherein target SWNTs are transferred into an aqueous phase for separation and extraction.

Surfactants are generally molecules having polar and non-polar ends and which commonly position at interfaces to lower the surface tension between immiscible chemical species. Surfactants can form micellular assemblies with the nanotubes in an appropriate solvent medium. In an aqueous system, the non-polar tail of the surfactant molecules will surround the nanotube, with the surfactant molecules radiating outward from the nanotubes like spokes on a wheel in a micellular-like fashion with the polar end groups on the outside of the micelle in contact with the aqueous media. Anionic, cationic or nonionic surfactants, with anionic and nonionic surfactants being more preferred, can be used in an appropriate solvent medium. Water is an example of an appropriate solvent medium.

Examples of anionic surfactants include, but are not limited to SARKOSYL® NL surfactants (SARKOSYL® is a registered trademark of Ciba-Geigy UK, Limited; other nomenclature for SARKOSYL NL surfactants include N-lauroylsarcosine sodium salt, N-dodecanoyl-N-methylglycine sodium salt and sodium N-dodecanoyl-N-methylglycinate), polystyrene sulfonate (PSS), sodium dodecyl sulfate (SDS), sodium dodecyl sulfonate (SDSA), sodium alkyl allyl sulfosuccinate (TREM) and combinations thereof. A preferred anionic surfactant that can be used is sodium dodecyl sulfate (SDS).

Examples of cationic surfactants that can be used, include, but are not limited to, dodecyltrimethylammonium bromide (DTAB), cetyltrimethylammonium bromide (CTAB), cetyltrimethylammonium chloride (CTAC) and combinations thereof. An example of a preferred cationic surfactant that can be used is dodecyltrimethylammonium bromide.

Examples of nonionic surfactants that can be used to disperse nanotubes in a solvent include, but are not limited to, SARKOSYL® L surfactants (also known as N-lauroylsarcosine or N-dodecanoyl-N-methylglycine), BRIJ® surfactants (BRIJ® is a registered trademark of ICI Americas, Inc.; examples of BRIJ surfactants are polyethylene glycol dodecyl ether, polyethylene glycol lauryl ether, polyethylene glycol hexadecyl ether, polyethylene glycol stearyl ether, and polyethylene glycol oleyl ether), PLURONIC® surfactants (PLURONIC® is a registered trademark of BASF Corporation; PLURONIC surfactants are block copolymers of polyethylene and polypropylene glycol), TRITON®-X surfactants (TRITON® is a registered trademark formerly owned by Rohm and Haas Co., and now owned by Union Carbide; examples of TRITON-X surfactants include, but are not limited to, alkylaryl polyethether alcohols, ethoxylated propoxylated $C_8$-$C_{10}$ alcohols, t-octylphenoxypolyethoxyethanol, polyethylene glycol tert-octylphenyl ether, and polyoxyethylene isooctylcyclohexyl ether), TWEEN® surfactants (TWEEN® is a registered trademark of ICI Americas, Inc; TWEEN surfactants include, but are not limited to, polyethylene glycol sorbitan monolaurate (also known as polyoxyethylenesorbitan monolaurate), polyoxyethylene monostearate, polyoxyethylenesorbitan tristearate, polyoxyethylenesorbitan monooleate, polyoxyethylenesorbitan trioleate, and polyoxyethylenesorbitan monopalmitate), polyvinylpyrrolidone (PVP) and combinations thereof. Preferred nonionic surfactants that can be used are alkylaryl polyethether alcohols, commercially known as TRITON-X® surfactants.

Other surfactants that can be used in accordance with the subject invention include, but are not limited to N-alkyl-amines such as N-alkyl-surfactant amine (e.g., octadecylamine (ODA)); primary, secondary, and tertiary amines with varying numbers of carbon atoms and functionalities in their surfactant alkyl chains (e.g., butyl-, sec-butyl-, tert-butyl-, pentyl-, hexyl-, heptyl-, octyl-, nonyl-, decyl-, dodecyl-, tetradecyl-, hexadecyl-, eicosadecyl-, tetracontyl-, pentacontyl-amines, 10,12-pentacosadiynoylamine, 5,7-eicosadiynoylamine, and combinations comprising one or more of the foregoing amines); and alkyl-aryl amines (e.g., benzyl amine, aniline, phenethyl amine, N-methylaniline, N,N-dimethylaniline, 2-amino-styrene, 4-pentylaniline, 4-dodecylaniline, 4-tetradecylaniline, 4-pentacosylaniline, 4-tetracontylaniline, 4-pentacontylaniline, and combinations comprising one or more of the foregoing amines).

To ensure selectively functionalized SWNTs are separable in a two-phase liquid system, active moieties (such as ionizable moieties) are added to the selectively functionalized SWNTs. As understood by the skilled artisan, ionizable moieties can be introduced either to nanotubes directly or to the selective functionalizing groups via any number of conventional chemical reactions. In one embodiment, reactants used to add ionizable moieties to functionalized nanotubes and improve functionalized SWNT extraction from non-functionalized SWNTs are preferably strong acids, and more preferably strong sulfonic acids. Contemplated strong acids for introduction of ionizable moieties include, but are not limited to, chlorobenzenesulfonic acid groups, hydrochloric acid, hydrofluoric acid, nitric acid, trifluoromethane sulfonic acid, concentrated sulfuric acid, fluorosulfuric acid, chlorosulfonic acid, methane sulfonic acid, oleum, and combinations thereof.

Figure 4A:
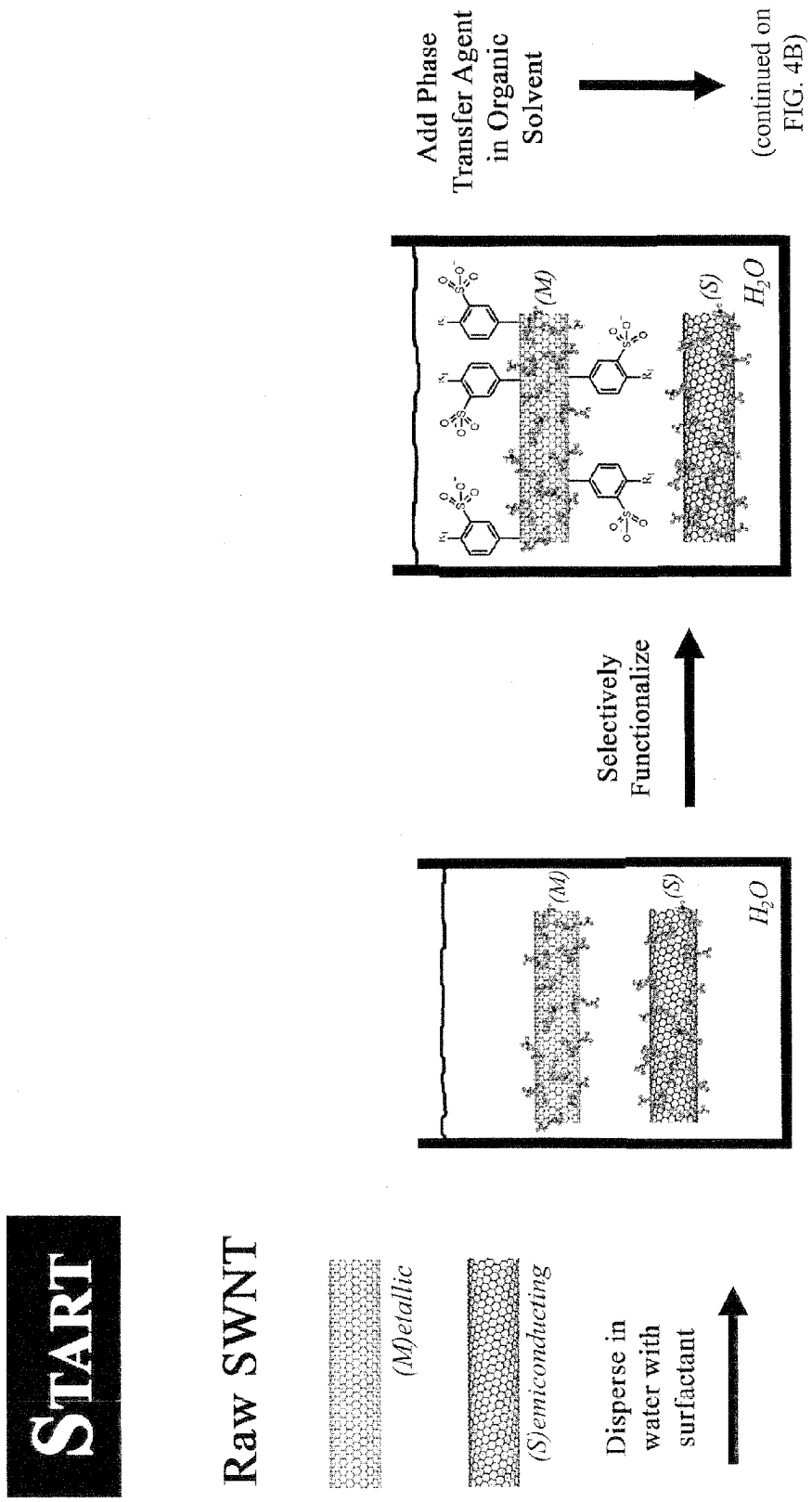
FIGS. 4A-4C constitute an illustration of the extraction process for a two-phase liquid-liquid extraction in accordance with the subject invention.
Figure 4B:
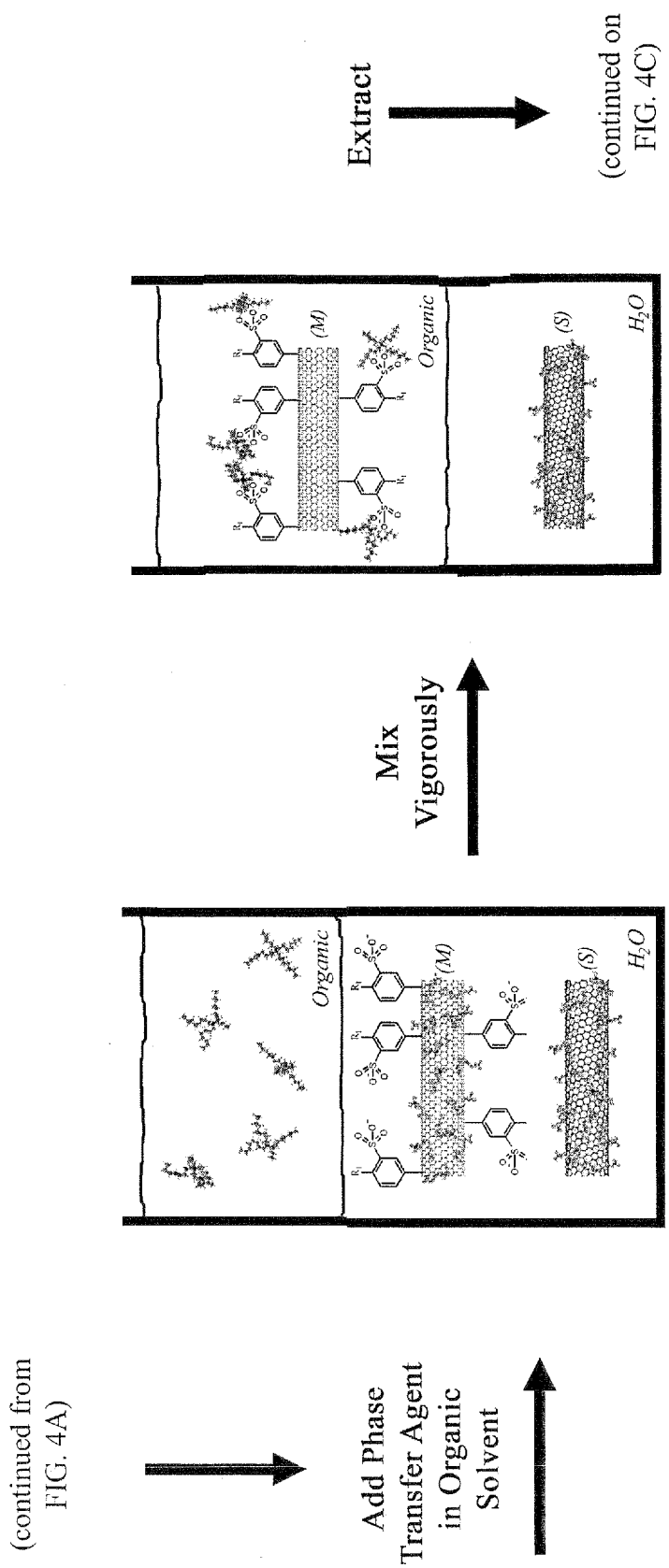
Figure 4C:
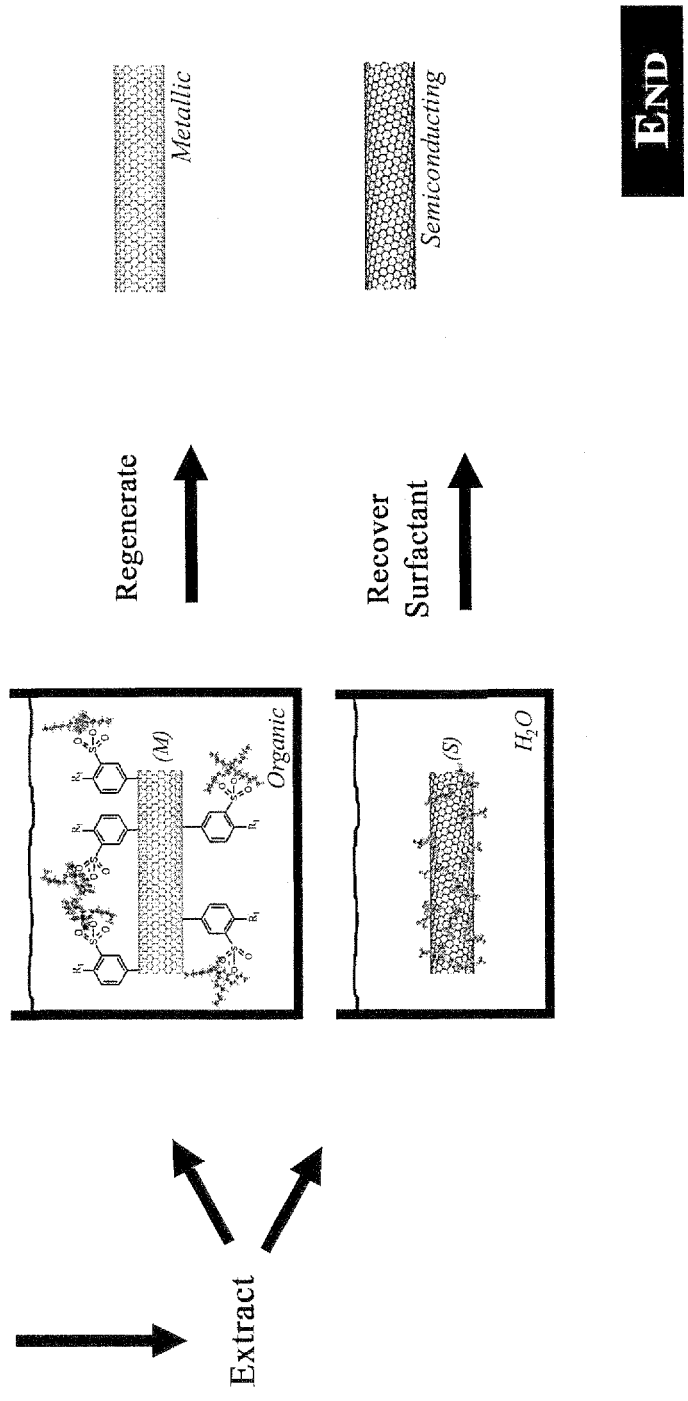

As illustrated in FIG. 1, upon addition of the active moiety (i.e., ionizable moiety—sulfonate anion), the selectively functionalized nanotubes (with diazonium agent) of the invention have high dispersibility in water (0.20 mg/L) and other polar solvents (e.g., methanol, ethanol). In one embodiment, the functionalized nanotubes (with ionizable and electron withdrawing moiety) are dissolved in a polar solvent (water) and placed in an extraction vessel. Then, a non-polar phase is prepared, wherein this phase is comprised of a non-polar solvent and phase transfer agent. In certain embodiments, the non-polar phase comprises a solution of tetraoctylammonium bromide (TOAB), a common phase transfer catalyst (agent), and an organic solvent (e.g., ethyl acetate or toluene). After agitation, SWNTs by type (i.e., metallic and semi-metallic SWNTs) are extracted into the non-polar phase and separated. The phase transfer agent is stripped from the nanotubes using organic solvents (such as acetic acid) and can be recycled for the separation of another target sub-population of functionalized SWNTs (i.e., metallic/semi-metallic SWNTs). In certain embodiments, after phase transfer agent stripper is added to the extraction vessel, a phase transfer agent is once again added to the vessel to further separate and extract functionalized SWNTs by type. The collected SWNTs are then subjected to pyrolysis to remove the functional groups are restore the original conjugated state of the SWNTs (see also FIGS. 4A-4C).

Figure 2:
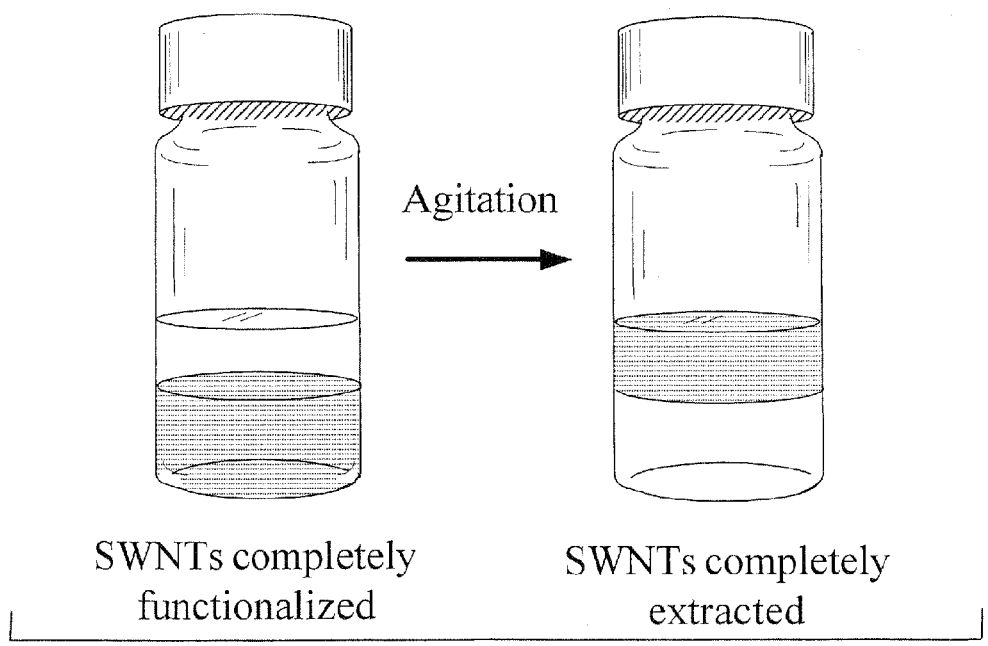
FIG. 2 is an illustration of the functionalization phase and extraction phase of one embodiment of the invention.

As illustrated in FIG. 2, the non-polar phase solution is added to the extraction vessel resulting in a two-phase (or liquid-liquid) phase system. The extraction vessel is shaken or stirred vigorously to increase interfacial area and assist transfer across the interface. The resultant mixture is filled with gray emulsions.

Polar solvents that can be used in accordance with the subject invention include, but are not limited to, water, methanol, ethanol, propanol, iso-propanol, formic acid, formamide, acetonitrile, N,N-dimethylformamide, diemthyl sulfoxide, ammonia, and combinations thereof. Non-polar solvents that can be used in accordance with the subject invention include, but are not limited to, ethyl acetate, toluene, chloroform, benzene, methylene chloride, tetrahydrofuran, diethyl ether, hexane, and combinations thereof.

When ethyl acetate is used as the non-polar (or organic) solvent, the emulsions are very fine with the swollen water phase occupying almost the entire liquid volume. The emulsions settle slowly and the presence of carbon, metallic/semi-metallic nanotubes is evident in the upper phase.

The extraction process is capable of many variations. There are a wide range of phase transfer catalysts that can be added to a non-polar solvent to form the non-polar phase. Contemplated phase transfer agents include, but are not limited to, quaternary onium salts, ammonium salts (such as Benzyl Triethyl Ammonium Chloride (BTEAC), Benzyl Trimethyl Ammonium Chloride (BTMAC), Cetyl Pyridinium Chloride (CPC), Cetyl Trimethyl Ammonium Bromide (CTAB), Phenyl Trimethyl Ammonium Chloride (PTMAC), Tetrabutyl Ammonium Bromide (TBAB), Tetrabutyl Ammonium Fluoride (TBAF), Tetrabutyl Ammonium Hydrogen Sulfate (TBAHS), Tetraethyl Ammonium Bromide (TEAB), Benzyl Triethyl Ammonium Chloride (TEBA), Tetrahexyl Ammonium Bromide (THAB), Tetramethyl Ammonium Hydroxide (TMAOH), Tetraoctyl Ammonium Bromide (TOAB), Methyl Tricaprylyl Ammonium Chloride (TOMAC), and Tetrapropyl Ammonium Bromide (TPAB)), polyglycols and crown ethers (such as 18-crown-6; Aliplex DB186; Butyl Diglyme; Dibenzo-18-crown-6; Diethylene Glycol Dibutyl Ether; Diethylene Glycol Dimethyl Ether; Diglyme; Dipropylene Glycol Dimethyl Ether; Monoglyme; Polyethylene Glycol Dibutyl Ether; Polyglycol BB 300; Polyglycol DME 200; Polyglycol DME 250; Polyglycol DME 500; Polyglycol DME 1000; Polyglycol DME 2000; Monoethylene Glycol Dimethyl Ether; Tetraethylene Glycol Dimethyl Ether; Tetraglyme; Triethylene Glycol Dimethyl Ether; and Triglyme), phosphonium salts, cryptands, and the like. These phase transfer agents (or catalysts) can be asymmetric or symmetric.

The organic phase can be exchanged for virtually any solvent that has at least limited solubility of the phase transfer catalyst and results in extraction of the functionalized nanotubes. In fact, any two phase system may be utilized for the extraction of the SWNTs where the use of a phase transfer catalyst is utilized in transferring the SWNTs from one phase to another. Any number of common methods utilized to reduce emulsion formation or stability such as demulsifiers or centrifugation may also be utilized.

In one embodiment, the ionic surfactant used to stabilize the dispersion could also be utilized for the phase transfer agent. For example, a cationic surfactant could be used to disperse the SWNTs. Then, after selective functionalization, the cationic surfactant will ion-pair with the anionic moieties on the selectively functionalized group. This will result in micelle inversion allowing the effective transfer of the functionalized SWNTs to the organic phase.

Another variation on the two-phase liquid extraction process of the invention is the use of SWNTs functionalized with functional groups in which reaction rates are diameter dependent. Functionalizing the SWNTs in such a fashion enables sorting and separation of SWNTs by diameter. After improving SWNTs' dispersibility in a polar phase (such as water using a surfactant and/or polymer) and selectively functionalizing the SWNTs by utilizing a diameter-dependent reaction with a selective functionalizing group, an active moiety (such as an anionic group or other ionizable moiety) is added to the sidewall of the nanotube. Subsequently, the polar phase comprising the functionalized nanotubes is combined with a non-polar phase comprising a phase transfer agent. Sorting, separation, and extraction procedure is easily carried out thereafter since the transfer phase agent (such as $TOA^+$) readily complexes with the active moieties (such as anionic groups: carboxylate and/or sulfonate anions).

Another variation on the two-phase liquid extraction process of the invention is the use of SWNTs functionalized with functional groups in which reaction rates are (n, m) dependent. Functionalizing the SWNTs in such a fashion enables sorting and separation of SWNTs by specific chiralities. After improving SWNTs' dispersibility in a polar phase (such as water using a surfactant and/or polymer) and selectively functionalizing the SWNTs by utilizing a chirality-dependent reaction with a selective functionalizing group, an active moiety (such as an anionic group or other ionizable moiety) is added to the sidewall of the nanotube. Subsequently, the polar phase comprising the functionalized nanotubes is combined with a non-polar phase comprising a phase transfer agent. Sorting, separation, and extraction procedure is easily carried out thereafter since the transfer phase agent (such as $TOA^+$) readily complexes with the active moieties (such as anionic groups: carboxylate and/or sulfonate anions).

According to the subject invention, the extraction of SWNTs from the water phase to the organic phase is reversible. After the extraction the anionic moiety on the functional group of the SWNTs are complexed with $TOA^+$ cations, thereby, making the composite dispersible in the organic phase. These cationic ligands can be de-complexed with the addition of excess acetic acid allowing recovery of the phase transfer agent. In the presence of excess acetic acid, the $TOA^+$ will preferentially bind to the acetate anions. The mixture is then filtered, the solids are placed in water, methanol, or ethanol and sonicated for ~1 minute to obtain re-suspension in the polar solvent. The functional groups on the sidewall can be removed by pyrolysis in an inert gas, thereby, returning the SWNTs to their original pristine state. Other chemical reactions could also be utilized to obtain the conjugated SWNT state.

The subject invention provides a scalable process for separating individual carbon nanotubes to yield new compositions of matter with new properties. The new matter consists of macroscopic amounts of type-sorted single-walled carbon nanotubes. Generally, macroscopic amounts of type-selected nanotubes could comprise at least about 15% of a selected type of nanotube, i.e., a particular individual (n, m) nanotube type, electronic properties (such as metallic versus semiconducting), or a particular nanotube diameter. Preferably, a macroscopic amount would comprise at least about 30% of a particular individual (n, m) nanotube type. More preferably, the macroscopic amount would comprise at least about 50% of a particular individual (n, m) nanotube type. More preferably, the macroscopic amount would comprise at least about 70% of a particular individual (n, m) nanotube type. More preferably, the macroscopic amount would comprise at least about 90% of a particular individual (n, m) nanotube type. In one embodiment, the type-selected nanotubes would have a narrow range of electronic properties or the range of properties could be tuned by strategically combining certain amounts of selected types of nanotubes.

Applications for Type-Separated Nanotubes

The availability of single-walled carbon nanotube samples based on (n, m) type, metallic versus semiconducting nature, or diameter is essential to many specialized applications. One such application is molecular electronics, in which a nanotube of a specific band gap may be needed as a wire to make an electrical connection. Similar electronic applications involve the use of nanotubes as field emission devices. Type specific SWNTs are also essential for biological applications such as imaging and sensing. Nanotubes of specific type can yield unique fluorescence which can be designed to interact with analytes for sensors or target cells to serve as biological markers. Yet another application requiring SWNTs of specific type is scanning probe microscopy where they are used as scanning probe tips.

The type specific SWNTs of the invention are particularly useful in high volume applications such as composite materials where the properties of the material derive at least in part from the properties of the type-selected nanotubes. Examples include electrically- and thermally-conductive polymer composites as well as materials with electrical or electromagnetic response(s) that are derived, at least in part, from the properties of the type-selected nanotubes. Another application enabled by this invention is the large-scale fabrication of electrical and electronic circuitry utilizing type-selected single wall carbon nanotubes. The availability of macroscopic amounts of type-specific nanotube material enables mass-production of nanometer-scale electronic circuitry. Specific type-selected single-wall carbon nanotubes can serve as an element of one or more electronic devices, including, but not limited to, interconnections between other devices, resistors, capacitors, diodes, transistors, pass elements, transducers, attenuators, heat transfer devices, memory elements, antennas, thermoelectric devices, piezoelectric devices, microwave circuitry, directional couplers, optoelectronic devices, electrochemical devices, fuel cell electrodes, fuel cell membranes, photoelectric cell electrodes, photoelectric cell active elements, circuit substrates, and heat conduction elements associated with electronic circuitry.

A. Fibers or Wires

With macroscopic amounts of metallic nanotubes separated in accordance with the subject invention, the metallic nanotubes could be aligned and made into conducting fibers or nanotube wires, the conductivity of which could favorably compete with copper. A fiber or nanotube wire of a rope or bundle of nanotubes would be conducting if any of the nanotubes in the bundle were metallic and contacted metallic tubes along the longitudinal axis of the rope or wire. Concentrations of metallic nanotubes of at least about 15% for such an application would be preferred. Accordingly, the subject invention provides methods for preparing compositions comprising at least about 15%, 30%, 50%, 70%, or 90%, or 99% metallic-type nanotubes. Examples involving methods for making nanotube ropes can be found in U.S. Pat. No. 6,183,714, which is incorporated herein in its entirety.

B. Nanotube Seeds

With macroscopic amounts of nanotubes separated by type in accordance with the subject invention, it is possible to use the type-selected nanotubes as seeds for growing even more of any selected nanotube type. An example of a process for growing nanotubes from nanotube seeds can be found in International Patent Publication No. WO 02/079082, which is incorporated herein in its entirety. By applying the type-selected nanotube compositions of the invention to the techniques disclosed in the International Publication, bulk production of type-selected single-wall carbon nanotubes can be accomplished.

C. Sensors

The capability of using the near-IR region of the electromagnetic spectrum to identify selected nanotubes opens a wide variety of previously unknown applications, devices, and uses for nanotubes involving sensing and monitoring carbon nanotubes as a function of their chemical and physical environment. In contrast to metallic nanotubes, which do not luminesce, semiconducting nanotube types are able to absorb radiation and luminesce in the near-IR. Note that luminescence can encompass fluorescence, phosphorescence, photoluminescence, other forms of optical emission, thermoluminescence, electroluminescence and combinations thereof. For semiconducting nanotubes, the diameter and chirality of the nanotube determine the electronic band-gap and hence the wavelength at which the nanotube will absorb incident photons and exhibit photoluminescence. Because nanotube luminescence is highly dependent on the electronic environment of the nanotube, the semiconducting nanotubes are very sensitive probes for monitoring and sensing changed electronic or chemical environment for a wide variety of different applications and uses. Additionally, the semiconducting nanotubes can be derivatized in such a manner, such as on one or both ends with one or more functional groups, such that the nanotube preserves its electronic signature. The functionalized nanotubes, due to the luminescent properties of the semiconducting structure, can be used as indicators in systems where the functional group may congregate, react or be preferentially absorbed.

To optimize the use of type-selected nanotubes and provide for the rapid detection of the selected semiconducting nanotubes, the excitation and fluorescence emission frequencies have been correlated with Raman shifts using variable laser frequencies to determine the correspondence for each particular (n, m) tube type. Although the emission frequencies appear to be all in the near-IR portion of the electromagnetic spectrum (i.e., wavelengths in the range of 700 nm and 2000 nm), the excitation frequencies can range from the near-IR, through the visible (i.e., wavelengths in the range of 400 nm and 700 nm), and, even into the ultraviolet portion of the electromagnetic spectrum (i.e., wavelengths in the range of about 300 nm and about 400 could be used for excitation of some small diameter semiconducting nanotubes.). Details of the structure assignment determinations and theory are disclosed in Bachilo, et al., "Structure-Assigned Optical Spectra of Single-Walled Carbon Nanotubes," *Science*, 298:2361-2365 (2002), which is incorporate herein by reference in its entirety.

The semiconducting nanotubes' ability to fluoresce in the near-IR optical frequency range provides a highly versatile and rapid detection method, enabling new, far-reaching areas of sensing and detecting, even as a non-destructive, or minimally invasive, sensor in biological systems. One of the advantages of being able to use excitation radiation and detect emission radiation in the near-IR is the ability to penetrate biological systems so that probes, sensors and detectors with nanotubes can be used in biological systems, including cells, tissues, interfacial membranes, and even living organisms.

The spectral properties of the nanotubes, and particularly the luminescence properties, are highly sensitive to their nanoscale environment. Chemical adsorbates on the nanotubes can alter these spectral properties and, consequently, semiconducting SWNTs obtained in accordance with the subject invention provide a sensitive optical sensing means for adsorbed gases, liquids and solids. The nanotubes are responsive to chemically, as well as physically, bound substituents, and can be used to sense general conditions of their environment, such as, but not limited to, pH, temperature, flow, pressure and changes in fluid dynamics and composition. They can also receive optical excitation and deliver electronic and thermal energy to their environment, such as by electrical and/or thermal luminescence.

Due to their small nanometer size, type-selected semiconducting SWNTs obtained in accordance with the subject invention can be applied to a sensor device for use in sensing conditions via non-invasive or minimally invasive optical probes. A light source in the UV, visible or near-IR provides for excitation of the nanotubes. Preferably, the light source is in the near-IR. The light source can be conducted by an optical fiber. The emitted or light returning from the nanotubes is detected by wavelength sensitive means and is subjected to spectral analysis. The spectral information obtained in turn provides information about the nanotubes and the chemical and physical environment.

In one embodiment, semiconducting SWNTs obtained in accordance with the subject invention are suspended in a liquid inside a vessel such as, but not limited to, a capillary flow tube or mixing chamber in a microfluidics device. The vessel is fitted with a window or structure transparent to light, including that of the near infrared. A light source, such as a conventional source, or a laser, such as a diode laser, is used to deliver light to the vessel containing the suspended semiconducting SWNTs via optical fibers and/or conventional optics. As light strikes the nanotubes, the nanotubes absorb some of the light, and the semiconducting nanotubes become luminescent and emit fluorescent light. The transmitted light also contains spectral information about the nanotube environment. The luminescent light is collected by optical fibers and/or conventional optics, and delivered to a spectrometer for spectral analysis. The various emitted wavelengths are detected and a spectrum is recorded in a computer. Similar apparatus setups can also be used to obtain spectral information from Raman scattering and from absorption spectral analysis.

In a related embodiment, an apparatus for detecting and sensing adsorbed and dissolved gases, such as carbon dioxide, is provided comprising type specific SWNTs (i.e., by diameter) obtained in accordance with the subject invention, which are dispersed in an aqueous media. A diode laser emitting red light in the range of 780 to 790 nm is transmitted by an optical fiber and focused into a vessel outfitted with an optically transparent means. Many silica-based glasses are suitable for this purpose. As with many molecular species, when carbon dioxide is present in the aqueous media, the fluorescence spectra being acquired will be altered. For lower concentrations, the longer wavelength emission derived from larger diameter nanotubes starts to diminish monotonically with increasing concentration of carbon dioxide. As the concentration increases, the longer wavelength fluorescence is extinguished. As the concentration of carbon dioxide further increases, the shorter wavelength fluorescence from the smaller diameter nanotubes starts to diminish. The signal intensities from the nanotubes are compared to a reference spectrum for nanotubes without the adsorbed gas. The concentration of the carbon dioxide adsorbate, or other gases or liquids, can then be determined. Since the spectral properties change as a water suspension of type specific SWNTs is exposed to varying levels of dissolved carbon dioxide, the nanotubes provide the basis for a quantitative sensor. Like devices and procedures can be used to measure the compositions of nanotube samples and the surrounding environmental conditions, such as, but not limited to factors of acidity, concentrations of dissolved gases, liquids, and solids, temperature, etc.

A type specific SWNT sensor can be used as a chemical "nose" to monitor adsorbates such as ozone, carbon dioxide, ammonia, halogens, nitrogen oxides, oxygen, and other rather reactive species that can also be environmental pollutants in air and water. The SWNT sensors can also be used in micro-reactor, microfluidic, microelectronic applications, as cellular based chemical sensors, sensors in lipid bilayers, sensors at catalyst surfaces, sensors attached or interacting with enzymes. Furthermore, the SWNT sensors can be used to monitor dissolved liquids, especially those prone to electron donor-acceptor bonding or hydrogen bonding, such as ketones, alcohols, ethers, carboxylic acids, esters, amides, hydroxyl-containing molecules, and substituted aromatic compounds. They can also be used to monitor dissolved or suspended solid materials such as polymers and to monitor the binding of metallic species which may also act as quenchers.

Some embodiments of the present invention are directed toward chemical applications where SWNT sensors provide an optical titration monitor as acid, base, or any other reactant is added and consumed. In other embodiments, the SWNT sensors provide an in-situ monitor to track reaction progress. In some embodiments of the present invention, a known variety of SWNT based on diameter size can be used as a multi-wavelength sensor for pH, flow, temperature, oxidation potential, and alterations due to exposure to light. In some embodiments, molecules that are not adsorbed on the nanotube can be detected by overtone quenching of the energy transfer between separated nanotubes. In yet another embodiment, the degree of alignment in a polymer by polarization of scattered light could be monitored using selected nanotubes as probes or polymer intercalants.

Methods of using SWNT sensors/probes can include biomedical applications. Such applications benefit from the fact that living tissue and cellular matter are essentially transparent to light with frequency in the near infrared (NIR). These methods are largely microscale applications of the chemical applications described above. These methods include measuring the change in fluorescence intensity and/or lifetime due to chromophores on adjacent proteins, nucleic acids other chromophores. Spectrally absorbing species, especially with large chromophores, such as those containing porphyrins will be detectable by the altered the fluorescence. Other biomedical applications involve cytometry type sorting based on the fluorescence signal. SWNTs in a droplet with adherent proteins, cells, etc. show a changed lifetime or intensity and may be selected and separated. In still other embodiments of the present invention, carbon nanotubes can be attached to a monoclonal antibody and luminescence spectroscopy can be used to monitor the degree of nanotube localization. A pulsed IR laser can then be used for selective thermal denaturation and localized damage to malignancies.

In embodiments of the present invention, carbon nanotubes can be used to measure surfactant concentration. Type specific nanotubes obtained in accordance with the subject invention can be used as monitors to yield very accurate information concerning drug delivery, transport and micelle interactions based upon the SDS response in these cases. In embodiments wherein the SWNT sensors are mounted on a porous membrane to create a flow-through device, the concentration of surfactant, counter-ions, and electrolyte in general can be detected continuously in real-time. This permits the monitoring of fluid mixing, flow, shear effects, laminar behavior, and gas flux across a membrane.

Additionally, other, more varied methods of using SWNT sensors of the invention include monitoring the efficacy of electrophoresis, electrostatic separation, chromatography, HPLC (High Performance Liquid Chromatography), supercritical fluid chromatography, gas chromatography, and magnetic chromatography; and using nanotubes individually or in thin films or fibers as electroluminescent sources for sensing, communications, or computing, and as photoconductive solids for optically active circuit elements for sensing applications. In other embodiments of the present invention, selected diameters and types of SWNTs are placed in a transparent matrix (such as polymers like PVP or glasses), or in a thin film, which can be used as fluorescent and absorption filters, especially in the near infrared, with the selection of nanotube types that determine the wavelength(s) that are transmitted. Such a filter made with a single type of SWNT with the corresponding absorption band can be used as a laser line blocker.

The SWNT sensors can also be dispersed individually in a liquid. They can also be made to "float" in a gaseous environment. In other embodiments, the SWNT sensors are "anchored" to a substrate in either a random or oriented manner. If oriented, they can be parallel to the substrate, perpendicular to the substrate, or combinations of the two. These can rely on only one nanotube or rely on a plurality of nanotubes. In methods of using the SWNT sensor devices of the current invention, there are many additional locations for the carbon nanotube sensors, such as: (a) fixed on the end of an optical fiber "optrode;" (b) fixed to electrical conductor and current source for electro-luminescence; (c) SWNTs bound to an electrode surface; (d) embedded in porous polymer matrix as support for liquid or gas (i.e., gases flowing through then alter the fluorescence as they adhere to the nanotubes and this will make the polymer more conductive if metallic tubes are used); (e) nanotubes on aerogels and low density supports for high surface area gas sensors, and (f) embedded in an inorganic (e.g., ceramic) matrix for high temperature sensors.

The small size, chemical inertness, and physical robustness of the carbon nanotubes makes these useful as in situ probes for micro- and nanoscale fluid containing devices, as well as for a living cell. When a transparent means is integral to the vessel being probed, such as a cell wall, then no additional transparent means need be added. In such circumstances, a single carbon nanotube may be sufficient as the sensor. The optical fiber may then be directly coupled to the vessel without an intervening lens. A single mode optical fiber provides the most effective delivery and return of light from a small volume, and in this case the same optical fiber can serve both functions. As an example of a microscale application, the "breathing" of a single cell might be monitored.

In embodiments of the present invention, the SWNT(s) may be anchored onto an end of an optical fiber, rather than being in suspension in the liquid being probed. In this form, it constitutes an "optrode," or optical sensing probe. A viable cell whose metabolism is altered by biological materials in the surrounding solution will change its generation of carbon dioxide and this can be sensed by the optrode. In this application, there may be clusters or aggregates of like SWNTs for increased sensitivity. It is preferable that aggregates of dissimilar nanotubes be kept separate to minimize energy transfer. Such aggregates should preferably be somewhat porous so as to allow intercalation and circulation of the fluid being probed. An alternative embodiment utilizes dissimilar, but non-quenching nanotubes to "funnel" excitation to one type of SWNT, as obtained in accordance with the subject invention, which will draw on the excitation energy of the surrounding nanotubes and will exhibit considerably enhanced signal, concentrated in a single wavelength peak, compared to its own excitation. This will allow the substitution of a single detector in place of the camera and disperser.

The optical device may also function on the principle of absorption, rather than emission. In these embodiments, the light source is broadband or "white light," rather than a laser. In some, the light passing through the optical fiber can undergo attenuated total internal reflection (ATR) in a prismatic means at the probe end of the optical fiber. Carbon nanotubes attached to or near the reflecting surfaces of the prism optrode absorb some of the wavelengths, which varies according to the type and concentration of adsorbates. The altered spectral signal returns up the optical fiber, and into a spectrometer means, and the signal is processed in a computer. The type and concentration of dissolved matter in the fluid is then determined. The ATR surface may comprise part of the fluid enclosure of the vessel, or may have a biological cell(s) attached to it, or it may be placed in contact with tissue that have nanotubes incorporated.

In certain embodiments, the probe may be an optical fiber with the light propagating in the core and the cladding thinned or removed to allow an evanescent wave to propagate into the medium to be probed. The signal light passes back into the source optical fiber, or an adjacent optical fiber. The optical fiber has nanotubes either attached to its surface, or in the surrounding medium to be monitored. The light conducting means may also be hollow or tubular, with a fluid flowing through and at least partially surrounded by the evanescent wave of the excitation light.

In further embodiments, the nanotubes may also provide a light source in the near infrared. Thin film assemblies of like nanotubes can be made to provide narrowband infrared luminescence with an electric current. The luminescence wavelength will correspond to that seen for optically excited fluorescence. Mixtures of nanotube types can alter the spectral emission. These devices can provide useful light sources for sensing, optical communication, and computing applications. They comprise a tunable or wavelength adjustable infrared laser source. Excitation of such light sources can be by laser, lamp, LED illumination, or electro-luminescence or direct electrical excitation from an alternating, inductively coupled, or direct current passing through the SWNT. Use of shorter wavelength lasers, such as the frequency-doubled Nd:YAG laser at 532 nm, and the argon ion at 514 or 488 nm enhances the sensitivity to metallic SWNTs. Pulsed illumination or high frequency modulation will be utilized for lifetime measurements.

In other embodiments, light and heat may be used to clean and restore the sensing capability on the nanotubes. For many of these cases, ultraviolet and/or light flash desorption can remove adsorbates. Carbon nanotubes and light can be used to generate gases, such as hydrogen, and promote boiling.

Besides single-wall carbon nanotubes, nanotube separation and sensors based on near-IR absorption and fluorescence should be considered to be applicable to few-wall and/or multiwall carbon nanotubes, as well as other nanotubes with extensive pi cloud conjugation, such as those made of boron nitride. Double-wall carbon nanotubes are an example of a multiwall carbon nanotube. In this case, there is a statistical probability of $1/5$th that both nanotube shells will be metallic, $4/5$ths that both shells will be semiconducting, and $4/5$ths that one shell will be semiconducting and one shell metallic. Nanotubes with at least one metallic tube $5/5$ths of total) are expected to behave like metallic nanotubes and not exhibit fluorescence, leaving $4/5$ths of the total having the possibility of exhibiting near-IR fluorescent behavior. The economics and availability of double-wall nanotubes and other multiwall nanotubes could provide cost-effective sensors for certain sensor applications.

The following examples are provided to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

Figure 3:
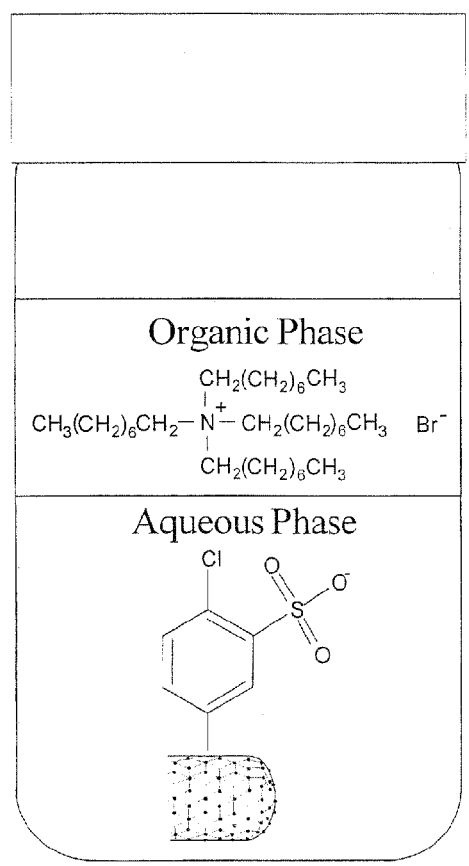
FIG. 3 is an illustration of a two-phase liquid system comprising an organic phase and aqueous phase in accordance with the subject invention.
Figure 5:
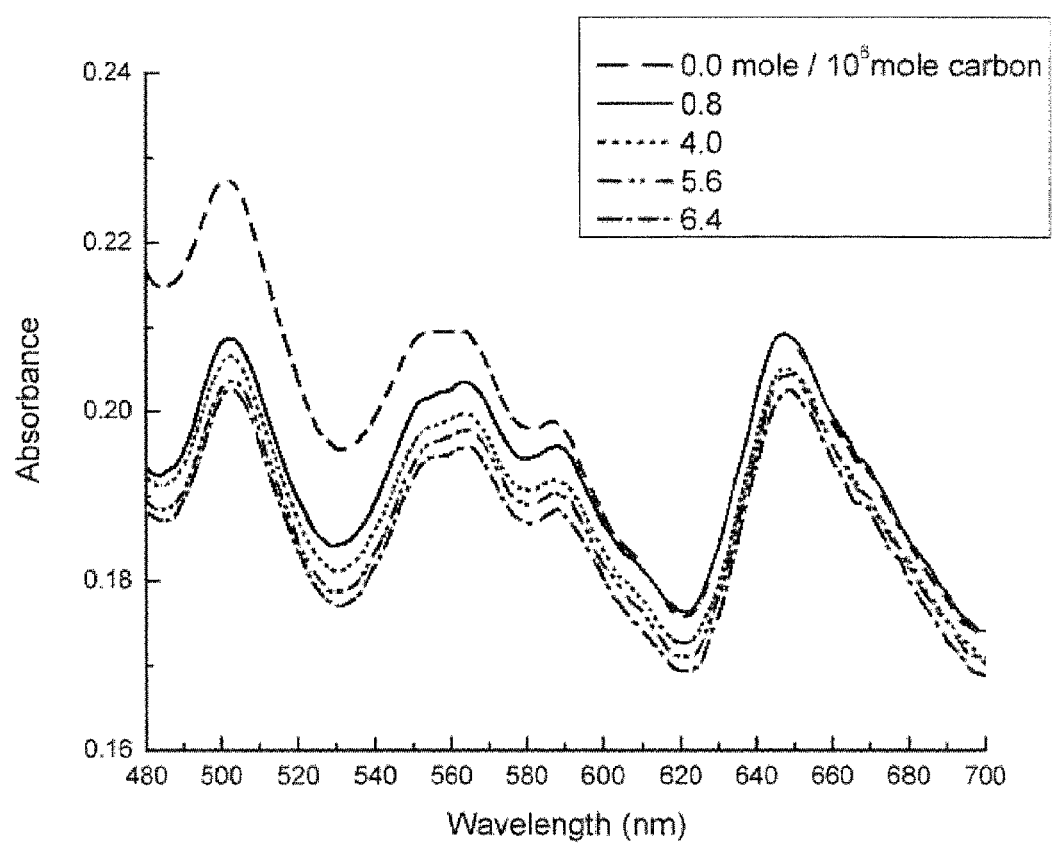
FIG. 5 is an illustration of the UV-vis-NIR absorbance spectra of the metallic nanotubes following selective functionalization.
Figure 6:
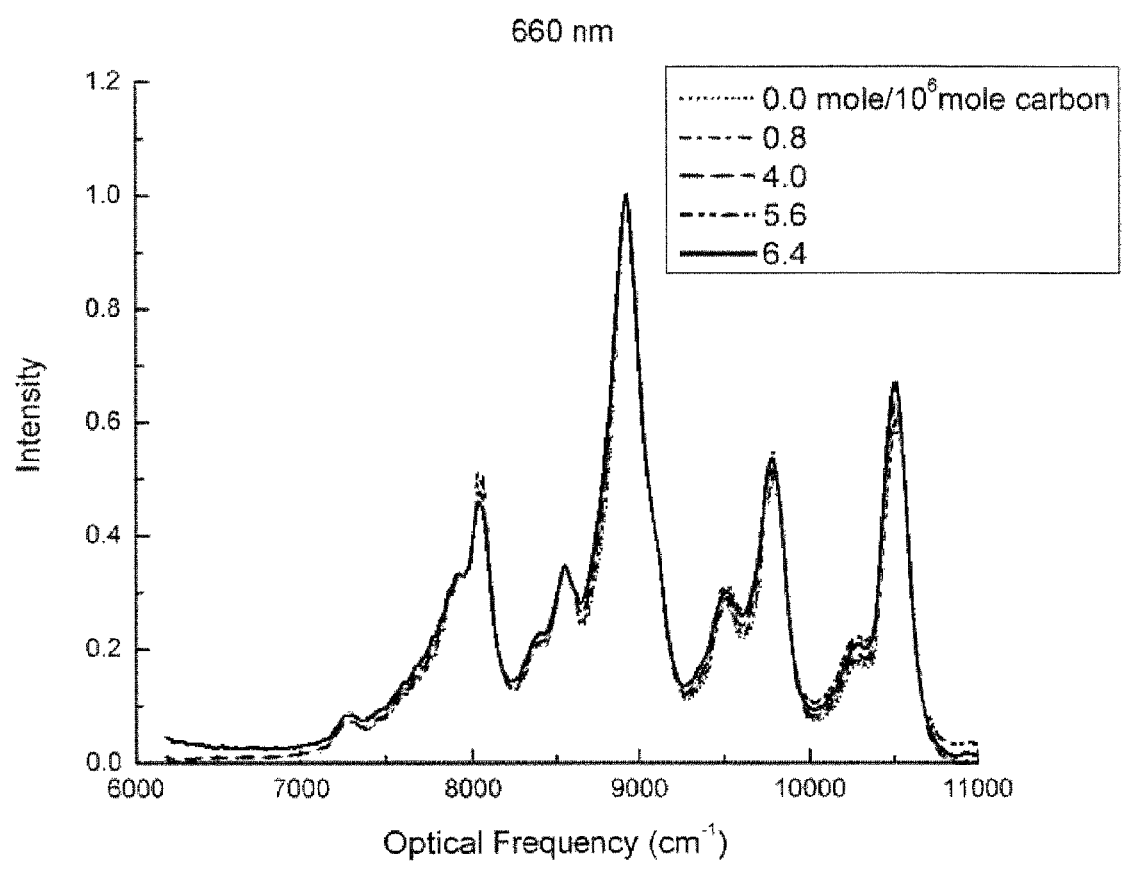
FIG. 6 is an illustration of the fluorescence spectra of semiconducting nanotubes excited with a 660 nm laser. Note that the spectra shows little changes confirming the selective functionalization.
Figure 7:
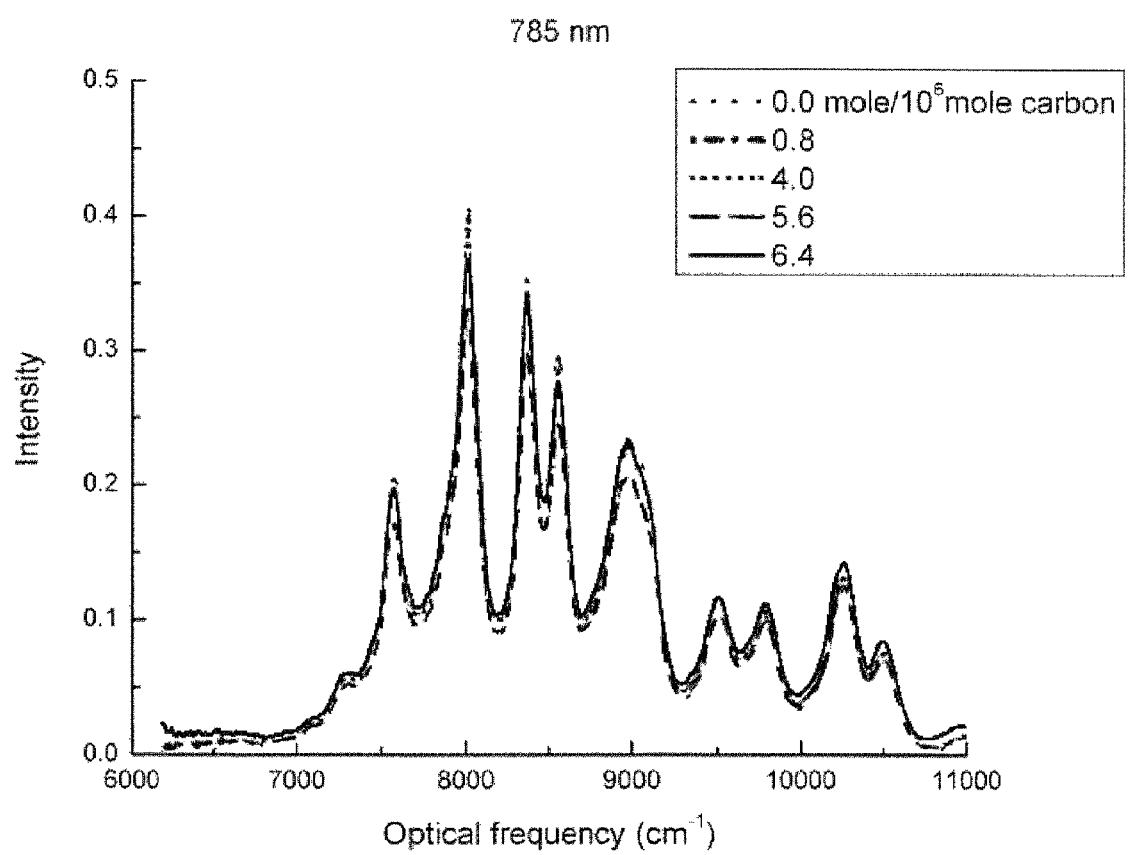
FIG. 7 is an illustration of the fluorescence spectra of semiconducting nanotubes excited with a 785 nm laser. Note that the spectra shows little changes confirming the selective functionalization.

HiPco single walled carbon nanotubes are suspended in water using SDS surfactant by mild sonication. The SWNTs are reacted with 4-chlorobenzenediazonium tetrafluoroborate until the band structure, as witnessed by UV-vis-NIR (see FIG. 5), of all metallic and semi-metallic nanotubes have dissipated while the fluorescence peaks associated with semi-conducting nanotubes show no appreciable changes (see FIGS. 6 and 7). The arene-functionalized nanotubes (present on the metallic and semi-metallic nanotubes only) are then further reacted with concentrated sulfuric acid to introduce a sulfonate group onto the benzene ring onto the arene-functional group. To this water phase, an organic layer consisting of a phase transfer agent, tetraoctyl ammonium bromide, dissolved in ethyl acetate is added forming a two-phase mixture (see FIG. 3). The two-phase mixture is vigorously agitated to increase interfacial area and allowed to settle for approximately 15 minutes. The ammonium cation has an electrostatic interaction with the anionic sulfonate moiety on the arene-functional group. With sufficient complexation and organic nature of the complexed metallic and semi-metallic nanotubes, the complexed SWNTs are dispersible in the organic phase and can be transferred across the phase boundary. However, the semi-conducting nanotubes will remain in the water phase since they have not been functionalized by the 4-chlorobenzenediazonium tetrafluoroborate chemistry.

As illustrated in FIG. 1, the organic phase containing the metallic and semi-metallic SWNTs is decanted to remove the metallic/semi-metallic SWNTs from the semi-conducting SWNTs. Glacial acetic acid is added to the metallic and semi-metallic SWNTs to strip the tetraoctyl ammonium ions from the nanotubes resulting in flocculation of the collected SWNTs. The tetraoctyl ammonium ions are regenerated to tetraoctyl ammonium bromide. The flocculated SWNTs are pyrolyzed in pure nitrogen at 300° C. to remove the aryl moieties from the sidewall and restore the conjugated state of the nanotubes.

EXAMPLE 2

HiPco single walled carbon nanotubes are suspended in water using Triton-X series surfactants by mild sonication. 4-chlorobenzenediazonium tetrafluoroborate is altered to introduce a sulfonate group onto the benzene ring. The SWNTs are reacted with this diazonium salt until the band structure, as witnessed by UV-vis-NIR, of all metallic and semi-metallic nanotubes have dissipated. To this water phase, an organic layer consisting of a phase transfer agent, tetraoctyl ammonium bromide, dissolved in ethyl acetate is added forming a two-phase mixture. The two-phase mixture is vigorously agitated to increase interfacial area and allowed to settle for approximately 15 minutes. The ammonium cation has an electrostatic interaction with the anionic sulfonate moiety on the arene-functional group. With sufficient complexation and organic nature of the complexed metallic and semi-metallic nanotubes, the complexed SWNTs are dispersible in the organic phase and can be transferred across the phase boundary. However, the semi-conducting nanotubes will remain in the water phase since they have not been functionalized by the 4-chlorobenzenediazonium tetrafluoroborate chemistry.

The organic phase containing the metallic and semi-metallic SWNTs is decanted to remove the metallic/semi-metallic SWNTs from the semi-conducting SWNTs. Glacial acetic acid is added to the metallic and semi-metallic SWNTs to strip the tetraoctyl ammonium ions from the nanotubes resulting in flocculation of the collected SWNTs. The tetraoctyl ammonium ions are regenerated to tetraoctyl ammonium bromide. The flocculated SWNTs are pyrolyzed in pure nitrogen at 300° C. to remove the aryl moieties from the sidewall and restore the conjugated state of the nanotubes.

EXAMPLE 3

HiPco single walled carbon nanotubes are suspended in water using SDS surfactant by mild sonication. The SWNTs are reacted with ozone which is believed to generate epoxide or ozonide groups on the nanotube sidewall. These epoxide or ozonide groups can be transformed to other functional groups by the addition of hydrogen peroxide ($H_2O_2$), dimethyl sulfide (DMS), and sodium borohydride ($NaBH_4$) in independent runs to selectively functionalize SWNTs by diameter to introduce an ionizable group onto the nanotube. See methods disclosed by Banerjee, S. and Wong, S. (for example, "Demonstration of Diameter-Selective Reactivity in the Sidewall Ozonation of SWNTs by Resonance Raman Spectroscopy," *Nano Letters*, 4(8):1445-1450 (2004); and "Rational Sidewall Functionalization and Purification of Single-walled Carbon Nanotubes by Solution-phase Ozonolysis," *J. Phys. Chem. B*, 106(47), 12144-12151 (2002), both of which are incorporated herein by reference in their entirety). To this water phase, an organic layer consisting of a phase transfer agent, tetraoctyl ammonium bromide, dissolved in ethyl acetate is added forming a two-phase mixture. The two-phase mixture is vigorously agitated to increase interfacial area and allowed to settle for approximately 15 minutes. The ammonium cation has an electrostatic interaction with the anionic sulfonate moiety on the oxidative sidewall-functionalized nanotubes. With sufficient complexation and organic nature of the functionalized nanotubes, the functionalized SWNTs are dispersible in the organic phase and can be transferred across the phase boundary. However, the non-functionalized nanotubes will remain in the water phase since they have not been functionalized by ozonolysis chemistry.

These examples serve to illustrate a typical extraction procedure in accordance with some embodiments of the present invention.

All patents, patent applications, and publications referred to or cited herein are incorporated by reference in their entirety, including all figures and tables, to the extent that they are not inconsistent with the explicit teachings of this specification.

I claim:

1. A two-phase liquid extraction method for separating nanotubes by type, said method comprising:
    a) dispersing a population of nanotubes in a liquid polar solvent to form a polar phase;
    b) selectively functionalizing a subpopulation of nanotubes from step (a) with a functionalizing group that enables the subpopulation of nanotubes to transport from a polar phase into a non-polar phase, and adding an active moiety to the sidewall of the functionalized nanotube subpopulation to assist in preferential transport from the polar phase into the non-polar phase;
    c) combining a liquid non-polar solvent with the liquid polar solvent to form a two-phase liquid mixture, wherein the non-polar solvent forms the non-polar phase; and
    d) agitating the two-phase mixture to increase interface area between the polar and non-polar phase and affect the preferential transport of the functionalized subpopulation of nanotubes into the non-polar phase.

2. The method of claim 1, further comprising the step of identifying the target subpopulation of nanotubes to be selectively functionalized.

3. The method of claim 1, where the functionalizing group is covalently bonded to the nanotubes.

4. The method of claim 1, where the functionalizing group is non-covalently bonded to the nanotubes.

5. The method of claim 1, wherein the active moiety is an ionizable moiety, and wherein the ionizable moiety is added by reacting the subpopulation of functionalized nanotubes with a sulfonic acid.

6. The method of claim 5, wherein the sulfonic acid is chlorobenzene sulfonic acid.

7. The method of claim 1, wherein the active moiety is an ionizable moiety, and wherein the ionizable moiety is added by reacting the subpopulation of functionalized nanotubes with sulfuric acid and oleum.

8. The method of claim 1, further comprising the step of dissolving a phase transfer agent in the non-polar solvent to form the non-polar phase to assist in the preferential transport of the targeted subpopulation of nanotubes.

9. The method of claim 8, wherein the phase transfer agent is tetraoctylammonium bromide.

10. The method of claim 1, wherein the agitation forms an emulsion in the non-polar phase, and wherein the method further comprises the step of adding a compound that serves to alter the stability of the emulsion formed during agitation.

11. The method of claim 10, wherein the compound is selected from the group consisting of SDS, SDBS, SDBA, CTAB, DTAB, Brij, Triton, Pluronics, and combinations thereof.

12. The method of claim 1, wherein the nanotubes are single-walled carbon nanotubes.

13. The method of claim 1, wherein the nanotubes are separated by their (n, m) type, wherein the (n,m) type is selected from the group consisting of conductivity, chirality, electronic properties, and diameter.

14. The method of claim 1, wherein the metallic and semi-metallic nanotubes are separated from semiconducting nanotubes.

15. The method of claim 14, wherein the metallic and semi-metallic nanotubes are transported into the non-polar phase.

16. The method of claim 1, wherein the nanotubes are separated by diameter or band gap.

17. The method of claim 1, wherein selective functionalization is achieved using water dispersible electron withdrawing moieties.

18. The method of claim 17, wherein the water dispersible electron withdrawing moiety is diazonium salt.

19. The method of claim 1, wherein the polar solvent is water.

20. The method of claim 1, wherein the non-polar solvent is selected from the group consisting of ethyl acetate, toluene, chloroform, benzene, methylene chloride, tetrahydrofuran, diethyl ether, hexane, and combinations thereof.

21. The method of claim 1, wherein the agitation is accomplished by vigorous shaking or stirring.

22. The method of claim 1, further comprising the step of adding a flocculating agent to the non-polar phase.

23. The method of claim 22, wherein the flocculating agent is acetic acid.

* * * * *

UNITED STATES PATENT AND TRADEMARK OFFICE
CERTIFICATE OF CORRECTION

PATENT NO. : 8,703,092 B2  Page 1 of 1
APPLICATION NO. : 12/066301
DATED : April 22, 2014
INVENTOR(S) : Kirk Jeremy Ziegler It is certified that error appears in the above-identified patent and that said Letters Patent is hereby corrected as shown below:

In the Specification
Column 1,
Line 44, "When the" should read --When n=m, the--.

In the Claims
Column 20, Claim 6
Line 29, "chiorobenzene" should read --chlorobenzene--.

Signed and Sealed this
Second Day of September, 2014

Michelle K. Lee
*Deputy Director of the United States Patent and Trademark Office*